United States Patent [19]

Marcilly

[11] 4,112,008

[45] Sep. 5, 1978

[54] PROCESS FOR ALKYLATION-TRANSALKYLATION OF AROMATIC HYDROCARBONS BY MEANS OF METHANOL

[75] Inventor: Christian Marcilly, Montesson, France

[73] Assignee: Institut Francais du Petrole, Rueil-Malmaison, France

[21] Appl. No.: 782,880

[22] Filed: Mar. 30, 1977

[30] Foreign Application Priority Data

Mar. 30, 1976 [FR] France .................. 76 09568

[51] Int. Cl.$^2$ ............... C07C 3/52; C07C 3/62
[52] U.S. Cl. ............... 260/671 M; 260/671 C; 260/672 T
[58] Field of Search ........... 260/671 M, 671 C, 672 T

[56] References Cited

U.S. PATENT DOCUMENTS

| | | | |
|---|---|---|---|
| 3,173,855 | 3/1965 | Miale et al. ............ | 260/672 T |
| 3,281,483 | 10/1966 | Benesi et al. ............ | 260/671 R |
| 3,316,317 | 4/1967 | Benesi ............ | 260/671 R |
| 3,377,400 | 4/1968 | Wise ............ | 260/672 T |
| 3,437,709 | 4/1969 | Chloupek ............ | 260/672 T |
| 3,631,120 | 12/1971 | Eberly et al. ............ | 260/671 R |
| 3,784,621 | 1/1974 | Suggitt ............ | 260/672 T |
| 3,962,363 | 6/1976 | Mabille et al. ............ | 260/671 M |

*Primary Examiner*—Delbert E. Gantz
*Assistant Examiner*—C. E. Spresser
*Attorney, Agent, or Firm*—Millen & White

[57] ABSTRACT

Process for alkylating or alkylating-transalkylating a charge containing toluene, methanol and, optionally, polymethylbenzenes, in one or two steps, conducted at a temperature from 100° to 600° C under a pressure from 1 to 150 bars in the presence of hydrogen and of a catalyst having a zeolite base of the faujasite type selected from Y sieves containing less than 2% by weight of sodium and at least 0.5% by weight of nickel, silver, cadmium or a mixture thereof and in which the molar ratio $SiO_2/Al_2O_3$ is from 2 to 6, and also in the presence of sulfur either introduced into the charge or preintroduced into the catalyst or both.

18 Claims, No Drawings

PROCESS FOR ALKYLATION-TRANSALKYLATION OF AROMATIC HYDROCARBONS BY MEANS OF METHANOL

The present invention concerns a new process for alkylating and transalkylating aromatic hydrocarbons, whereby xylenes can be obtained selectively by reaction or combination of reactions involving toluene, methanol and, optionally, one or more polymethylbenzenes.

It is known that xylenes, particularly orthoxylene and more particularly paraxylene, are presently of common use for the manufacture of resin fibers (e.g. "tergal"), polyester films and plastics.

The more interesting xylenes, orthoxylene and paraxylene, can be obtained by conversion of various aromatic hydrocarbons such as, in particular, toluene, metaxylene and trimethylbenzenes. Among these operations the most usual are:

(1) alkylation of toluene by means of methanol, (2) transalkylation of toluene by means of trimethylbenzenes, (3) dismutation of toluene producing, on the one hand, xylenes and, on the other hand, benzene, in substantially equal amounts, (4) isomerization of metaxylene and ethylbenzene.

Another more complex reaction involving the use of a mixture of methanol, toluene and $C^+_9$ polymethylbenzenes ($C^+_9$ = hydrocarbons having 9 carbon atoms per molecule or more) may also be used for the synthesis of xylenes.

The present invention concerns generally the alkylation of toluene by means of methanol and also the complex reaction of alkylation-transalkylation making use of the toluene-methanol-$C^+_9$ polymethylbenzenes mixture, in the presence of very suitable catalysts particularly favoring these reactions. The $C^+_9$ polymethylbenzenes may be, for example, trimethylbenzenes, tetramethylbenzenes, pentamethylbenzenes, hexamethylbenzene, condensed methylaromatic hydrocarbons, condensed polymethyl aromatics or complex molecules a part of which is a methylbenzene or a polymethylbenzene or a condensed polymethylaromatic hydrocarbon.

It is known that the above-mentioned reactions which are considered according to the present invention are speeded up by the presence of acid catalysts. The most conventional acid catalysts are amorphous silica-aluminas, zeolites, silica-magnesias, silica-zirconias, boria-aluminas, alumina-magnesias, catalysts of the FRIEDEL-CRAFT type, etc . . . It is also known that, although any acid catalyst may be used, the preferred catalysts are however those favouring alkylation reactions as compared to dismutation reactions of aromatics.

It has now been discovered that the catalysts used according to the present invention are exclusively zeolites of the faugasite structure, preferably Y sieves, in which the larger part of the sodium ions contained in said zeolites have been exchanged with ions selected from at least ions of metals from group VIII, particularly nickel, group Ib, particularly silver, and group IIb, particularly cadmium. These zeolites whose pore openings are of the order of 8 to 10 Angstroms, i.e. large enough to give passage to the molecules of condensed polymethylbenzenes or to complex molecules as above described, originally contain sodium cations.

These zeolites contain sodium ions having no catalytic activity or only a small activity. It is thus necessary to remove the cations at least partially and to replace them by other cations imparting to the zeolite a good activity. These sieves are accordingly exchanged so as to remove at least 50% and preferably at least 80% of the alkali metal cations. The replacement may be performed by ammonium ions which can be either decomposed, by heating, to gaseous ammonia, which escapes from the structure, and to $H^+$ protons, which remain inside the structure as compensation cations, or exchanged with cations of the desired metals. Multivalent metal cations may also be introduced into the structure by direct exchange of the general alkali ions. In the case, for example, of Y sieves, there can be introduced into the structure, by means of one of the preceding methods, for example, metals selected from alkaline earth metals or rare earths or from various transition metals of groups VIII, Ib and IIb. However, it has been discovered, according to the present invention, that the introduction, by exchange, into Y zeolites, of ions from metals of group VIII, such as nickel, and/or of group Ib, such as silver, and/or group IIb, such as cadmium, provides for a very substantial improvement of activity, said activity being maintained during time for alkylation reactions making use of toluene, methanol and optionally at $C^+_9$ polymethylbenzene.

These preferred metals may, as above-described, be introduced directly in replacement of the original sodium ions. They may also be introduced in replacement of the ammonium ions or of other multivalent ions (alkaline-earth or rare earths) with which the zeolite has been previously exchanged.

In the case of cadmium and particularly of silver for which the faujasite structure has a particularly high affinity, the ion exchange may be conducted directly on the sodium form of the zeolite up to substantially complete replacement of sodium ions by silver or cadmium ions. Such an exchange is not possible with nickel since the exchange is limited to 70–75% of the sodium ions and the 25 to 30% of the sodium ions remaining in the zeolites impart to the latter a poor catalytic activity. With nickel it is thus preferred to replace in a first step the major part of the sodium ions by ammonium ions and to proceed in a second step to the exchange with nickel ions.

For improving the thermal stability of the zeolite it may be preferably to introduce into the latter, during the ion exchange, ions of alkaline-earth metals such as magnesium, or rare-earth metals such as lanthanum or cerium. Such metals are known to increase the acidity and the thermal stability of the zeolite structure. Their content in the final catalyst must then be higher than about 0.01% by weight.

During the ion exchange, particular attention must be paid to the pH of the solutions contacted with the zeolite. Solutions of acid pH are liable to damage the structure. The stability of the faujasite structure is contact with an acid solution depends on the ratio $SiO_2/Al_2O_3$; thus the Y sieve structure having a ratio $SiO_2/Al_2O_3$ of about 5 is quickly destroyed at a pH below 3. Whereas it is possible to easily adjust the pH of nickel solutions, even concentrated ones, for example 1 mole per liter, to a value ranging from about 5 to 7, such an adjustment cannot be achieved with silver without resulting in the precipitation of the corresponding hydroxide. In the case of the latter metal, the exchange will thus be preferably performed with a solution to which is added a sufficient ammonia amount to precipitate the silver hydroxide and then to dissolve it again in the form of an ammoniacal complex of the formula $Ag(NH_3)_2^+$. Exchange with the ammoniacal complex may also be performed in the case of cadmium and of nickel.

In all cases, the residual sodium current must not exceed 2.0% by weight of the zeolite and, preferably, not exceed 1.5% by weight and the content in metals from groups VIII, I$b$, II$b$ must not be lower than 0.5% by weight.

The maximum content in metals from groups VIII, I$b$ and II$b$ are of the order of 30%. The metal content depends in fact on the experimental conditions of the catalyst manufacture. This content may, a priori, be indifferently low or high. However, it has been observed that the selectivity is improved with contents closer to the minimum of 0.5% then to the maximum of 30%, the activity being however, as an average, of the same order of magnitude irrespective of the metal content. The molar ratio $SiO_2/Al_2O_3$ of the zeolite ranges from about 2 to 6, preferably from about 3 to 6.

The exchanged zeolites are dried at a temperature, for example, from 80° to 150° C in a hot-air oven and then calcined at 250° to 600° C in the presence of air. Before being used, they are reduced in the presence of hydrogen at a temperature from 250° to 550° C. The resulting catalysts have also a more or less substantial hydrogenation power with respect to aromatic hydrocarbons; this tendency is still enhanced in the presence of methanol and/or steam. It has also been discovered that it is necessary to neutralize said hydrogenation power by sulfurizing the metal or metals of the zeolite. Such a sulfurization may be achieved in two ways:

(1) Either before the catalytic reaction, by treating the catalyst with a stream of hydrogen sulfide and hydrogen. In this case, the operation is such that the catalyst, before use, has a sulfur content advantageously from 0.1 to 15% by weight, and more particularly from 0.5 to 12%, with respect to the catalyst.

(2) Or by adding to the initial charge, at the beginning of the reaction, a sulfur compound such as dimethyldisulfide, thiophene, benzothiophene, a mercaptan etc... The operation is such that the charge preferably contains from 0.001 to 5% by weight of sulfur compound and more particularly from 0.05 to 5% of said sulfur compound.

According to a preferred method, it is advantageous to proceed by combining these two methods, i.e. by pretreating the catalyst with a mixture of hydrogen and hydrogen sulfide and introducing a sulfur compound into the charge.

Moreover it is advantageous to add to the charge, continuously during the reaction, a small amount of sulfur so as to maintain sufficient sulfurization of the metal of the catalyst. There is thus advantageously added to the charge from 0.03 to 0.3% of sulfur compound by weight with respect to the charge, for example about 0.1%. The operation is so conducted as to obtain a charge containing preferably, during the reaction, from about 0.001 to 5%, more particularly 0.05 to 5% by weight of sulfur compound.

It has been unobviously observed, in addition, that this sulfurization, useful when proceeding, according to the invention, with nickel, silver and cadmium catalysts, does not result in any improvement when using catalysts of the Y sieve type, free of nickel, silver or cadmium.

The alkylation or alkylation-transalkylation of the aromatic hydrocarbons may be conducted at will in the presence or the absence of a dilution gas such as hydrogen or an inert gas (nitrogen, argon etc . . .). The presence of hydrogen is preferred according to the invention.

The presence of the reactants in a single vapor phase is preferred according to the invention. The vaporized charge is passed through a reactor in which the catalyst is, for example, in the form of a fixed bed. However, it is also possible to proceed with a fluid or moving bed.

The operating conditions of the process of the invention are as follows:

– The molar composition of the two types of charge, toluene-methanol or toluene-methanol-$C^+_9$ polymethylbenzene, is within the following ranges:

30 to 95% of toluene,
70 to 5% of methanol and preferably:

40 to 85% of toluene
60 to 15% of methanol or:

20 to 95% of toluene
2 to 60% of methanol
2 to 60% of $C^+_9$ polymethylbenzene and preferably:

30 to 85% of toluene
5 to 40% of methanol
10 to 40% of $C^+_9$ polymethylbenzenes The temperature is from 100° to 600° C, preferably from 200° to 500° C.

The pressures are in the range from 1 (atmospheric pressure) to 150 bars and preferably from 1 to 60 bars.

The feeding space velocity, expressed in volume of charge per volume of catalyst and per hour is from 0.05 to 10 and preferably from 0.1 to 5.

When proceeding in the presence of hydrogen, the molar ratio $H_2$/feed stock (or charge) is from 0.1 to 20 and preferably from 1 to 10.

The operating conditions must always be so selected as to permit preferably to proceed in the vapor phase.

The following examples are given for illustrative purpose and are not limitative.

Although in the examples and for sake of simplification, the various catalytic reactions has been performed in a single step in the vapor phase, it is also possible to proceed in two steps, the operating conditions in each of these two steps being the same as above indicated.

Each step is performed, according to the invention, in the presence of catalysts as above-defined and in the presence of sulfur. The second step may however be conducted in the vapor phase or the liquid phase.

The U.S. Pat. No. 3 962 363 shows how such a process has been performed in two steps, although the catalysts used in this U.S. patent are not the same as in the present case and sulfur is not used.

EXAMPLE 1 (FOR COMPARATIVE PURPOSE)

1 000 grams of hydrated Na-Y sieve of the trade, containing about 8% by weight of sodium (sold by Union Carbide Co. under reference SK 40), in which the ratio $SiO_2/Al_2O_3$ is about 5, is suspended in an aqueous solution of ammonium nitrate at a concentration of 3M, the volume of the solution corresponding to a quantity of ammonium ions amounting to 10 times the quantity of the sodium ions present in the zeolite mass. The solution is stirred and brought to 90° C to 6 hours. It is filtered and subjected again to two identical exchanges. After filtration the solid is washed. The resulting product, called $NH_4Y$ (zeolite Y containing ammonium ions) is not dried. The analysis indicates a sodium residual content of 1.3% by weight with respect to the solid calcined for 2 hours at 500° C.

EXAMPLE 2 (COMPARATIVE)

100 grams of the preceding product $NH_4$—Y are calcined at 550° C for 2 hours in the presence of air. There is obtained the solid NY (zeolite with $H^+$ ions), which does not conform to the catalyst used according to the invention.

EXAMPLE 3 (COMPARATIVE)

100 grams of the product $NH_4$—Y of example 1 is suspended in one liter of a solution adjusted to a pH of 6 and containing 0.25 mole of lanthanum nitrate. The solution is stirred and maintained at room temperature for 6 hours. The solid is then filtered, washed, dried at 100° C for 2 hours and calcined at 550° C for 2 hours in the presence of air. It is referred to as La HY (zeolite containing $H^+$ ions and lanthanum ions). % La = 11.1% by weight. It does not comply with the requirements of the catalyst used according to the invention.

EXAMPLE 4

100 grams of $NH_4$—Y of example 1 are exchanged twice successively in one liter of an aqueous solution containing one mole of nickel nitrate and 0.2 mole of lanthanum nitrate. The solution, whose pH is adjusted to 6, is stirred and maintained at room temperature for 6 hours. The solid, dried and calcined as in Example 3, is referred to as Ni La HY. This Y zeolite according to the invention contains 5.9% by weight of nickel and 5.5% by weight of lanthanum.

EXAMPLE 5

100 grams of $NH_4Y$ of example 1 are exchanged twice successively in one liter of an aqueous solution containing one mole of nickel nitrate. The solution is adjusted to a pH of 6.5 and maintained at room temperature for 6 hours. The solid, dried and calcined as in examples 3 and 4, is referred to as Ni—HY. Said Y zeolite according to the invention contains 7.5% by weight of nickel.

EXAMPLE 6

100 grams of $NH_4$—Y of example 1 are exchanged in one liter of aqueous solution containing one mole of silver nitrate to which has been added a sufficient amount of ammonia to produce the precipitation of silver hydroxide and then, a new solubilization of the latter. Said solution, whose pH value is about 10, is stirred and maintained at room temperature for 8 hours. The solid, dried and calcined as in examples 3, 4 and 5, is referred to as Ag HY. Said zeolite according to the invention contains 28.8% by weight of silver.

EXAMPLE 7

100 grams of $NH_4$—Y of example 1 are exchanged in one liter of an aqueous solution containing one mole of cadmium chloride, in conditions identical to those of example 6. The solid, dried and calcined as in the 4 preceding examples, is referred to as Cd HY. Said zeolite contains 12% by weight of cadmium.

EXAMPLE 8 (COMPARATIVE)

300 grams of sodium mordenite as extrudates of 1/16 inch, available on the trade under the trade mark "Zeolon 900 Na", manufactured by NORTON Company, are suspended in three liters of a solution containing two moles of ammonium nitrate. The solution, adjusted to a pH of 7, is stirred and maintained at room temperature for 6 hours. After filtration and washing, three identical new exchanges are performed. The solid, filtered and washed, is referred to as $NH_4M$(mordenite with ammonium ions). Its sodium content, determined on a few grams of the solid calcined at 500° C, is 0.26% by weight.

EXAMPLE 9 (COMPARATIVE)

100 grams of the solid $NH_4M$ of example 8 are dried at 100° C and then calcined at 550° C for 2 hours. This product is referred to as HM (mordenite $H^+$).

EXAMPLE 10 (COMPARATIVE)

100 grams of the solid $NH_4M$ of example 8 are suspended in one liter of a solution whose pH is adjusted to a value of 7 and which contains 1 mole of nickel nitrate. The solution, adjusted to a pH of 6, is stirred and maintained at room temperature for 6 hours. After filtration, a new identical exchange is performed. The product, filtrated, washed, dried at 100° C and calcined at 550° C for 2 hours, is referred to as NiHM (mordenite with nickel ions). Its nickel content is 2.1% by weight.

EXAMPLE 11 (COMPARATIVE)

100 grams of the solid $NH_4M$ of example 8 are suspended in one liter of a solution containing one mole of silver nitrate to which has been added a sufficient amount of ammonia to first precipitate the silver hydroxide and then again solubilize the latter. The pH is then close to 10. The stirred solution is maintained at room temperature for 6 hours. The product washed, filtered, dried at 100° C and calcined at 550° C for 2 hours, is referred to as Ag HM (mordenite with silver ions). Its silver content is 17.5% by weight.

These various catalysts, prepared according to examples 1 to 11, are subsequently subjected to alkylation or alkylation-transalkylation tests making use either of toluene and methanol or of a complex mixture of toluene-methanol-tetramethylbenzene. The following operating conditions are the same for all the tests:

P (bars) = 30 (except in example 17 in which the pressure is 50 bars)

Feed space velocity = 1 grams of charge/hour and gram of catalyst

Molar ratio $H_2$/charge = 5

The operation is conducted in the vapor phase in the presence of hydrogen.

EXAMPLE 12 (comparative)

This example relates to the alkylation of toluene by means of methanol over HY sieves of example 1 and La HY sieves of example 3.

There is prepared a charge No. 1 composed of 2 moles of toluene per mole of methanol. The tests have been conducted in the above mentioned conditions at the following temperatures: 250° C, 300° C, 350° C, 400° C. The results are reported in table I below. It should be noted that if these catalysts were used in the presence of sulfur as explained in example 14 for the catalysts used according to the invention, the results of table I would remain unchanged.

TABLE 1

| Catalyst | T° C | Aromatic yield % b.w.* | Composition of the aromatics (%mole) | | | | | | |
|---|---|---|---|---|---|---|---|---|---|
| | | | benzene | toluene | PX | MX | OX | TMB | $T_4MB$ ** | Other arom. *** |
| HY | 250 | 100 | 0.1 | 97.2 | 1.05 | 0.95 | 0.4 | 0.25 | 0.01 | 0.01 |
| | 300 | 99.5 | 0.1 | 92.1 | 2.3 | 2.4 | 0.9 | 1.8 | 0.3 | 0.1 |
| | 350 | 97.8 | 0.6 | 87.3 | 3.0 | 4.1 | 1.9 | 2.1 | 0.7 | 0.3 |
| | 400 | 97.9 | 0.9 | 80.1 | 4.2 | 6.9 | 3.1 | 3.1 | 0.9 | 0.8 |
| La HY | 250 | 100 | 0.2 | 97.0 | 1.04 | 0.97 | 0.5 | 0.2 | 0.01 | 0.01 |
| | 300 | 99.0 | 0.3 | 91.2 | 2.9 | 2.8 | 1.0 | 1.5 | 0.1 | 0.15 |
| | 350 | 98.2 | 0.7 | 86.5 | 3.1 | 4.5 | 1.9 | 2.3 | 0.6 | 0.4 |
| | 400 | 97.7 | 1.0 | 79.0 | 4.4 | 7.1 | 3.2 | 3.4 | 1.0 | 0.9 |

*The aromatic yield is expressed in % by weight with respect to toluene
**$T_4MB$ = tetramethylenes
***Other aromatics = aromatics other than benzene, toluene, paraxylene (PX), metaxylene (MX), orthoxylene (OX), trimethylbenzenes (TMB) and tetramethylbenzene ($T_4MB$).

EXAMPLE 13 (COMPARATIVE)

This example concerns the alkylation of toluene by means of methanol over NiLaHY sieves of example 4 and NiHM sieves of example 10 in the absence of sulfur.

The results obtained with these two catalysts on the same charge No. 1 and under the same conditions as above are reported in table II below.

TABLE II

| Catalyst | T° C | Aromatic yield % by weight |
|---|---|---|
| Ni La HY | 250 | 17 |
| | 300 | 12 |
| | 350 | 15 |
| Ni HM | 250 | 38 |
| | 300 | 40 |
| | 350 | 28 |
| | 400 | 47 |

It is apparent that the zeolite exchanged with nickel ions has a high hydrogenating power which results in a degradation of the aromatics and, accordingly, in a low yield of aromatic hydrocarbons. In order to reduce said hydrogenating power, the catalysts containing nickel, silver and cadmium have been tested subsequently on charge containing a small amount of sulfur in the form of dimethyl disulfide.

EXAMPLE 14

This example concerns the alkylation of toluene by means of methanol over Ni La HY sieves of example 4 and Ni HY sieves of example 5, in the presence of sulfur.

Before the proper alkylation test, the two catalysts are treated for 3 hours at 250° C with toluene containing 1% by weight of dimethyldisulfide. This treatment is conducted under a hydrogen pressure of 30 bars, with a molar ratio $H_2$/charge = 8 and a feed space velocity of 1 gram of charge per gram of catalyst and per hour. The resulting catalyst contains 0.25% of sulfur.

The proper alkylation test is conducted under the same conditions as above with a charge No. 2 containing 2 moles of toluene per mole of methanol and also containing 0.1% by weight of dimethylsulfide. The results are reported in table III below.

TABLE III

| Catalyst | T° C | Aromatic yield % b.w. | Composition of the aromatics (%mole) | | | | | | |
|---|---|---|---|---|---|---|---|---|---|
| | | | benzene | toluene | PX | MX | OX | TMB | $T_4MB$ | Other aromatics |
| Ni La HY | 250 | 98.6 | 0.05 | 86.2 | 2.8 | 4.9 | 2.1 | 2.3 | 0.8 | 0.8 |
| | 300 | 94.1 | 0.1 | 71.7 | 5.0 | 8.9 | 4.2 | 5.9 | 1.7 | 2.5 |
| | 350 | 92.7 | 0.5 | 53.0 | 7.8 | 15.1 | 7.0 | 9.9 | 2.8 | 3.9 |
| Ni HY | 250 | 97.9 | 0.08 | 86.3 | 2.9 | 5.1 | 2.2 | 2.1 | 0.7 | 0.6 |
| | 300 | 94.5 | 0.2 | 71.3 | 5.4 | 9.2 | 4.3 | 5.7 | 1.8 | 2.1 |
| | 350 | 92.8 | 0.6 | 54.7 | 7.8 | 15.0 | 6.8 | 9.5 | 2.5 | 3.1 |
| | 400 | 90.1 | 3.8 | 48.0 | 8.2 | 16.3 | 7.5 | 10.0 | 2.6 | 3.5 |

By comparison with table II it is observed that Y sieves containing nickel, used in the presence of sulfur, are much more selective than the same catalysts used in the absence of sulfur: the degradation of the aromatic rings indicated in table III is in fact very low as compared to those indicated in table II. It is also observed, by comparison with table I, that the Y sieves containing nickel are much more active than the Y sieves without nickel. Comparative example 18 shows that, under the operating conditions of said example 14, the catalyst Ni HM, with a mordenite base, gives less satisfactory results than in the present case with Ni La HY or Ni HY.

EXAMPLE 15

This example concerns the alkylation of toluene by methanol over Ag HY sieves of example 6 and Cd HY sieves of example 7.

These two catalysts are tested, under conditions identical to those of example 14, in the presence of sulfur introduced as mentioned in example 14. The results obtained are reported in Table IV.

TABLE IV

| Catalyst | T° C | Aromatic yield % b.w. | Composition of the aromatics (%mole) | | | | | | | |
|---|---|---|---|---|---|---|---|---|---|---|
| | | | benzene | toluene | PX | MX | OX | TMB | T₄MB | Other aroma. |
| Ag HY | 250 | 99.1 | 0.02 | 87.2 | 2.7 | 4.3 | 1.9 | 2.2 | 0.7 | 0.9 |
| | 300 | 97.0 | 0.1 | 77.0 | 4.1 | 7.2 | 3.3 | 4.6 | 1.5 | 2.1 |
| | 350 | 95.1 | 0.3 | 59.2 | 7.0 | 13.3 | 6.1 | 8.4 | 2.5 | 3.2 |
| Cd HY | 250 | 98.2 | 0.07 | 87.8 | 2.6 | 4.0 | 1.8 | 2.0 | 0.7 | 1.0 |
| | 300 | 96.0 | 0.15 | 75.8 | 4.0 | 7.8 | 3.4 | 4.8 | 1.6 | 2.4 |
| | 350 | 93.5 | 0.7 | 56.1 | 7.2 | 14.1 | 6.5 | 9.0 | 2.9 | 3.5 |

Here also there is observed an improved activity of Y sieves exchanged with silver and cadmium as compared to HY sieves. The activity of these two catalysts is however slightly lower than that of Ni HY and Ni La HY sieves.

EXAMPLE 16

This example concerns the alkylation-transalkylation of the toluene-methanol-tetramethylbenzene complex mixture over the Ni La HY sieve of example 4.

There is prepared a charge No. 3 whose molar composition is 12% of 1, 2, 4, 5 — T₄MB, 23% of methanol and 65% of toluene. The results of the test conducted with the Ni La NY catalyst under the same activating and operating conditions as in examples 14 and 15 (in the presence of sulfur introduced as in example 14: the catalyst contains 0.25% by weight of sulfur and the charge contains 0.1% by weight of dimethylsulfide) are reported in table V.

TABLE V

| Catalyst | T° C | Aromatic yield % b.w. | Composition of the aromatics (%mole) | | | | | | | |
|---|---|---|---|---|---|---|---|---|---|---|
| | | | benzene | toluene | PX | MX | OX | TMB | T₄MB | Other arom. |
| Ni La HY | 250 | 99.2 | — | 65.0 | 6.8 | 6.0 | 2.4 | 10.7 | 7.0 | 2.1 |
| | 300 | 96.1 | — | 44.2 | 12.1 | 13.3 | 4.8 | 17.4 | 5.8 | 2.4 |
| | 350 | 91.1 | — | 35.6 | 12.2 | 17.9 | 9.3 | 22.0 | 3.2 | 1.8 |

From these results it is apparent that Y sieve exchanged with nickel is very active in the reaction of alkylation-transalkylation making use of toluene, 1, 2, 4, 5-tetramethylbenzene and methanol. In addition, it is observed that the selectivities to paraxylene obtained at low conversion rates, are higher than those obtained under the same conditions in the alkylation of toluene-methanol.

EXAMPLE 17

This example concerns a long duration test of toluene-methanol alkylation on Ni La HY sieve of example 4.

This test has been performed over 50 days with a charge containing 2 moles of toluene per mole of methanol and 0.02% by weight of dimethyl-disulfide under the following conditions: T° C = 250 or 300° C, P = 50 bars, molecular ratio H₂/charge = 5, feeding space velocity: 1 gram of charge per hour and gram of catalyst. The operation is conducted in the vapor phase; the results are reported in table VI below.

TABLE VI

| T° C | time (days) | arom. yield (% b.w.) | Composition of the aromatics (% mole) | | | | | | | |
|---|---|---|---|---|---|---|---|---|---|---|
| | | | benzene | toluene | PX | MX | OX | TMB | T₄MB | other aromatics |
| 300 | 0.25 | 94.1 | 2.2 | 60.2 | 6.4 | 12.5 | 4.9 | 7.8 | 1.5 | 4.5 |
| 300 | 1 | 93.1 | 2.0 | 61.5 | 5.8 | 10.4 | 5.9 | 8.9 | 2.5 | 3.0 |
| 300 | 5 | 94.9 | 1.7 | 64.0 | 5.9 | 8.2 | 6.0 | 8.5 | 2.6 | 3.1 |
| 300 | 18 | 92.8 | 0.9 | 68.5 | 5.6 | 7.3 | 5.9 | 6.6 | 2.3 | 2.9 |
| 250 | 30 | 96.9 | 0.5 | 83.2 | 1.2 | 3.2 | 6.2 | 1.0 | 0.4 | 4.3 |
| 300 | 50 | 95.1 | 0.7 | 70.4 | 5.1 | 6.0 | 6.3 | 5.2 | 2.2 | 4.1 |

A test has been performed under identical conditions, except the temperature which was 350° C, on the La HY sieve of example 3, in order to compare the stability of this catalyst with that of the Ni La HY catalyst. After 5 days of test, the activity of the La HY catalyst is quite negligible; this activity is substantially the same as that of HY mentioned in example 12. The presence of nickel in the Y sieve thus considerably improves the activity and the stability of this sieve in the reaction of toluene alkylation by methanol although the coke content of the solid after 50 days of test is relatively high (about 10% by weight).

The selectivity, with respect to orthoxylene, of the Ni La HY catalyst in run, i.e. partially deactivated, is very substantial when the conversion rate is not too high. This result is quite unexpected. It is also to be observed that, if the operation had been conducted in the absence of dimethylsulfide, with the La HY catalyst, the results of the five days test would have been substantially the same.

EXAMPLE 18 (COMPARATIVE)

This example concerns the alkylation of toluene by methanol, making use of HM catalyst of example 9, Ni HM catalyst of example 10 and Ag HM catalyst of example 11.

These three catalysts have been tested under conditions identical to those of examples 14 and 15, in the presence of sulfur introduced as indicated in example 14.

The results obtained respectively at 300°, 350° and 400° C. are reported in table VII below.

TABLE VII

| Catalyst | T° C | Aromatic yield % b.w. | Composition of the aromatics (% mole) | | | | | | | |
|---|---|---|---|---|---|---|---|---|---|---|
| | | | benzene | toluene | PX | MX | OX | TMB | $T_4MB$ | Other aroma. |
| HM | 300 | 99.8 | 0.7 | 95.7 | 1.1 | 1.2 | 0.5 | 0.5 | 0.05 | 0.2 |
| | 350 | 99.4 | 1.0 | 92.0 | 1.9 | 2.4 | 0.9 | 1.3 | 0.2 | 0.3 |
| | 400 | 98.8 | 3.1 | 84.8 | 2.2 | 4.1 | 1.8 | 2.4 | 0.9 | 0.8 |
| Ni HM | 300 | 99.3 | 0.9 | 95.2 | 1.2 | 1.5 | 0.7 | 0.4 | 0.03 | 0.05 |
| | 350 | 99.3 | 3.9 | 85.5 | 2.1 | 3.5 | 1.6 | 1.9 | 0.7 | 0.8 |
| | 400 | 98.4 | 10.2 | 62.0 | 4.8 | 9.3 | 4.1 | 5.3 | 1.8 | 2.5 |
| Ag HM | 300 | 99.8 | 0.8 | 95.7 | 1.3 | 1.3 | 0.5 | 0.3 | 0.15 | 0.07 |
| | 350 | 99.1 | 3.6 | 86.3 | 2.2 | 3.3 | 1.4 | 1.7 | 0.8 | 0.7 |
| | 400 | 98.5 | 10.1 | 61.4 | 5.1 | 9.4 | 4.5 | 5.0 | 1.9 | 2.6 |

These results show that mordenites of H form or exchanged with Ni and Ag cations have alkylating properties substantially lower than those of Y sieves. Moreover, these catalysts, whose dismutation power is high, have a much lower activity than that of Y sieves.

What I claim is:

1. In a process for catalytically alkylating a charge containing from 30 to 95% by mole of toluene and 5 to 70% by mole of methanol in the presence of hydrogen, at a temperature from 100° to 600° C., under a pressure from 1 to 150 bars, with a feed space velocity, expressed in volume of charge per volume of catalyst and per hour, from 0.05 to 10, with a molar ratio $H_2$/charge from 0.1 to 20, wherein the improvement comprises conducting said alkylating in the presence of a catalyst having a zeolite base of the faujasite type selected from Y sieves containing less than 2% by weight of sodium and in which the molar ratio $SiO_2/Al_2O_3$ is from about 2 to 6, said catalyst containing at least 0.5% by weight of at least one metal selected from nickel, silver and cadmium, said catalyst having been calcined in the presence of air at 250°–650° C. and then reduced in the presence of hydrogen at 250°–550° C., said alkylating being performed in the presence of sulfur, said sulfur being introduced into the initial charge in such an amount that the latter contains from 0.001 to 5% by weight of a sulfur compound, and/or preintroduced into the catalyst in such an amount that the catalyst contains from 0.1 to 15% by weight of sulfur.

2. A process according to claim 1, conducted in the vapor phase.

3. A process according to claim 1 in which the catalyst is a zeolite selected from the Y sieves having a molar ratio $SiO_2/Al_2O_3$ from about 3 to 6, the catalyst containing less than 1.5% by weight of sodium, at least 0.5% by weight of at least one metal selected from nickel, cadmium and silver, and further containing at least 0.01% by weight of at least one additional metal selected from the metals of group IIa of the periodic classification and the lanthanides.

4. A process according to claim 3 in which the additional metal is lanthanum.

5. A process according to claim 4, in which the catalyst contains nickel.

6. A process according to claim 1, in which said metal is nickel.

7. A process according to claim 1, in which said metal is silver.

8. A process according to claim 1, in which said metal is cadmium.

9. A process according to claim 1, in which sulfur is both preintroduced into the catalyst and introduced into the initial charge and wherein, in addition, there is added continuously to the charge a sulfur compound in an amount from 0.03 to 0.3% with respect to said charge.

10. In a process for catalytically alkylating-transalkylating a charge containing from 20 to 95% by mole of toluene, 2 to 60% by mole of tetramethylbenzene and 2 to 20% by mole of methanol in the presence of hydrogen, at a temperature from 100° to 600° C., under a pressure from 1 to 150 bars, with a feed space velocity, expressed in volume of charge per volume of catalyst and per hour, from 0.05 to 10, with a molar ratio $H_2$/charge from 0.1 to 20, wherein the improvement comprises conducting said alkylating-transalkylating in the presence of a catalyst having a zeolite base of the faujasite type selected from Y sieves containing less than 2% by weight of sodium and in which the molar ratio $SiO_2/Al_2O_3$ is from about 2 to 6, said catalyst containing at least 0.5% by weight of at least one metal selected from nickel, silver and cadmium, said catalyst having been calcined in the presence of air at 250°–650° C. and then reduced in the presence of hydrogen at 250°–550° C., said alkylating-transalkylating being performed in the presence of sulfur, said sulfur being introduced into the initial charge in such an amount that the latter contains from 0.001 to 5% by weight of a sulfur compound, and/or preintroduced into the catalyst in such an amount that the catalyst contains from 0.1 to 15% by weight of sulfur.

11. A process according to claim 10, conducted in the vapor phase.

12. A process according to claim 10 in which the catalyst is a zeolite selected from the Y sieves having a molar ratio $SiO_2/Al_2O_3$ from about 3 to 6, the catalyst containing less than 1.5% by weight of sodium, at least 0.5% by weight of at least one metal selected from nickel, cadmium and silver, and further containing at least 0.01% by weight of at least one additional metal selected from the metals of group IIa of the periodic classification and the lanthanides.

13. A process according to claim 12 in which the additional metal is lanthanum.

14. A process according to claim 13, in which the catalyst contains nickel.

15. A process according to claim 10, in which said metal is nickel.

16. A process according to claim 10, in which said metal is silver.

17. A process according to claim 10, in which said metal is cadmium.

18. A process according to claim 10, in which sulfur is both preintroduced into the catalyst and introduced into the initial charge and wherein, in addition, there is added continuously to the charge a sulfur compound in an amount from 0.03 to 0.3% with respect to said charge.

* * * * *